(12) United States Patent
Zheng

(10) Patent No.: US 9,463,263 B2
(45) Date of Patent: *Oct. 11, 2016

(54) TENOCYTE CONTAINING BIOSCAFFOLDS AND TREATMENT USING THE SAME

(75) Inventor: Ming-Hao Zheng, City Beach (AU)

(73) Assignee: Orthocell Pty Ltd (AU)

( * ) Notice: Subject to any disclaimer, the term of this patent is extended or adjusted under 35 U.S.C. 154(b) by 715 days.

This patent is subject to a terminal disclaimer.

(21) Appl. No.: 12/597,127

(22) PCT Filed: Apr. 24, 2008

(86) PCT No.: PCT/AU2008/000583
§ 371 (c)(1),
(2), (4) Date: Apr. 15, 2010

(87) PCT Pub. No.: WO2008/128304
PCT Pub. Date: Oct. 30, 2008

(65) Prior Publication Data
US 2010/0233233 A1    Sep. 16, 2010

(30) Foreign Application Priority Data

Apr. 24, 2007  (AU) ............................. 2007902168
Mar. 26, 2008  (AU) ............................. 2008901451

(51) Int. Cl.
A61L 27/38 (2006.01)

(52) U.S. Cl.
CPC .......... *A61L 27/386* (2013.01); *A61L 27/3804* (2013.01); *A61L 27/3895* (2013.01); *A61F 2310/00365* (2013.01); *A61L 2430/10* (2013.01)

(58) Field of Classification Search
None
See application file for complete search history.

(56) References Cited

U.S. PATENT DOCUMENTS

| | | | |
|---|---|---|---|
| 4,668,233 | A | 5/1987 | Seedhom et al. |
| 4,775,380 | A | 10/1988 | Seedhom et al. |
| 4,902,508 | A | 2/1990 | Badylak et al. |
| 4,939,239 | A | 7/1990 | Matsuhashi et al. |
| 5,352,463 | A | 10/1994 | Badylak et al. |
| 5,842,573 | A | 12/1998 | Halvorsen |
| 6,368,298 | B1 | 4/2002 | Beretta et al. |
| 6,569,172 | B2 | 5/2003 | Asculai et al. |
| 2002/0173806 | A1 | 11/2002 | Giannetti et al. |
| 2003/0147935 | A1* | 8/2003 | Binette ............... A61F 2/0063 424/423 |
| 2004/0037812 | A1 | 2/2004 | Giannetti et al. |
| 2004/0078077 | A1 | 4/2004 | Binette et al. |
| 2004/0136968 | A1* | 7/2004 | Zheng ............... A61K 35/12 424/93.7 |
| 2004/0267362 | A1 | 12/2004 | Hwang et al. |
| 2005/0060033 | A1 | 3/2005 | Vacanti et al. |
| 2005/0113937 | A1 | 5/2005 | Binette et al. |
| 2005/0177249 | A1 | 8/2005 | Kladakis et al. |
| 2007/0004035 | A1* | 1/2007 | Sitzmann ................. 435/325 |
| 2007/0005139 | A1 | 1/2007 | Vacanti et al. |
| 2007/0162121 | A1 | 7/2007 | Tarrant et al. |
| 2007/0276509 | A1 | 11/2007 | Ratcliffe et al. |
| 2009/0093056 | A1* | 4/2009 | Itskovitz-Eldor et al. ... 435/372 |

FOREIGN PATENT DOCUMENTS

| | | |
|---|---|---|
| EP | 0223370 A2 | 5/1987 |
| EP | 1092436 A1 | 4/2001 |
| WO | WO 00/72782 A1 | 12/2000 |
| WO | WO 01/32229 A1 | 5/2001 |
| WO | WO 2004/022078 A1 | 3/2004 |
| WO | WO 2004/029230 A2 | 4/2004 |
| WO | WO 2004/093932 A1 | 11/2004 |
| WO | WO 2007106949 A1 * | 9/2007 |

OTHER PUBLICATIONS

Wong et al., "Triamcinolone Suppresses Human Tenocyte Cellular Activity and Collagen Synthesis," Clinical Orthopaedics and Related Research, No. 421, pp. 277-281 (2004).*
Merriam-Webster on-line dictionary. Definition of "deriviative.".*
Irakam et al., (Biology of the Neonate, vol. 82 pp. 89-95; 2002).*
Guner et al. (British Journal of Cancer, vol. 35, vol. 4, pp. 439-447; 1977).*
Qiu et al. (Cells Tissues Organs, vol. 197 pp. 27-26; 2013).*
Irakam et al., Biology of the Neonate, vol. 82 pp. 89-95; 2002 (of record).*
Guner et al., British Journal of Cancer, vol. 35, vol. 4, pp. 439-447; 1977(of record).*
Abrahamsson et al., Journal of Orthopaedic Research, vol. 9, pp. 495-502 (1991).*
Levine et al., The Journal of Cell Biology, vol. 100, pp. 1415-1422 (1985).*
Schulze-Tanzil et al. (Histochemistry and Cell Biology, vol. 122, pp. 219-228 (2004).*
Australian Patent Office website page for AU 2006901495; publication date Apr. 6, 2006. Publication date accessed on Dec. 3, 2015 at http://pericles.ipaustralia.gov.au/ols/auspat/applicationDetails.do?applicationNo=2006901495.*
Australian Patent Application AU 2006901495 priority document accessed from the WIPO Internation Bureau for PCT/AU2007/000362.*

(Continued)

Primary Examiner — Soren Harward
Assistant Examiner — Paul D. Pyla
(74) Attorney, Agent, or Firm — Baker & Hostetler LLP

(57) ABSTRACT

The present invention relates to methods for preparing bio scaffolds useful in the repair of tears. More specifically, the invention relates to a method of treating rotator cuff tear in a mammalian subject in need thereof comprising the steps of: (i) selectively expanding tenocytes in vitro in culture medium comprising insulin or a functional derivative and a glucocorticoid or a glucocorticoid-like molecule to produce a culture of expanded tenocytes; (ii) seeding a bioscaffold with said expanded tenocytes to produce a tenocyte seeded bioscaffold; and (iii) implanting said tenocyte seeded bioscaffold proximal to the rotator cuff tear. The present invention also relates to a bioscaffold comprising cells, wherein more than 80% of said cells are tenocytes.

26 Claims, 16 Drawing Sheets

(56) References Cited

OTHER PUBLICATIONS

Amstutz et al., "Reconstruction of the Canine Achilles and Patellar Tendons Using Dacron Mesh Silicone Prosthesis. I. Clinical and Biocompatibility Evaluation", J. Biomed. Mater. Res., 1976, 10(1), 47-59.
Androjna et al., "Mechanical Conditioning of Cell-Seeded Small Intestine Submucosa: A Potential Tissue-Engineering Strategy for Tendon Repair," Tissue Engineering, Feb. 2007, vol. 13, No. 2, pp. 233-243, Abstract.
Bigliani et al., "Operative Treatment of Failed Repairs of the Rotator Cuff", J. Bone Joint Surg. Am., Dec. 1992, 74(10), 1505-1515.
Briner et al., "Common Injuries in Volleyball. Mechanisms of Injury, Prevention and Rehabiliation", Injury Clinic., 1997, 24(1), 65-71.
Burkhart et al., "A Stepwise Approach to Arthroscopic Rotator Cuff Repair Based on Biomechanical Principles", Arthroscopy: The Journal of Arthroscopic and Related Surgery, Jan.-Feb. 2000 16(1), 82-90.
Calleja et al., "The Antibiotic Rifampicin is a Nonsteroidal Ligend and Activator of the Human Glucocorticoid Receptor", Nat. Med., Jan. 1998, 4(1), 92-96.
Chan et al., "Insulin-through the ages: Phylogeny of a growth promoting and metabolic regulatory hormone", American Zoologist, 2000, 40, 213-222.
Fini et al., "In Vitro Study Comparing Two Collageneous Membranes in View of Thief Clinical Application for Rotator Cuff Tendon Regeneration", J. of Orthopaedic Research, Jan. 2007, vol. 25, No. 1, 98-107.
Gerber et al., "Experimental Rotator Cuff Repair. A Preliminary Study", J. Bone Joint Surg. Am., Sep. 1999, 81(9), 1281-1290.
Grandhi et al., "A Comparative Pharmacological Investigation of Ashwagandha and Ginseng", J. Ethnopharmacol., 1994, 44, 131-135.
Hattrup, "Rotator Cuff Repair: Relevance of Patient Age", J. Shoulder Elbow Surg., Mar./Apr. 1995, 4(2), 95-100.
Iannotti, "Full-Thickness Rotator Cuff Tears: Factors Affecting Surgical Outcome", J. Am. Acad. Orthop. Surg., Mar./Apr. 1994, 2(2), 87-95.
Marsh, "Preparation and Properties of Allergoids, Derived From Native Pollen Allergens by Mild Formalin Treatment", Int. Arch. of Allergy and Appl. Immunol., 1971, 41, 199-215.
Mazzocca et al., "Tendon and Bone Responses To a Collagen-Coated Suture Material," Journal of Shoulder and Elbow Surgery, Sep.-Oct. 2007, vol. 16, No. 5 Suppl, pp. 222S-230S.
Movin et al., "Tendon Pathology in Long-Standing Achillodynia, Biopr findings in 40 patients", Acta Orthop Scantd, 1997, 68 (2): 170-175.
Schulze-Tanzil et al., "Cultivation of Human Tenocytes in High-Density Culture," Histochemistry and Cell Biology, Jul. 2004, vol. 122, No. 3, pp. 219-228, Abstract.
Shalabi et al., "Dynamic Contrast-Enhanced MR Imaging and Histopathology in Chronic Achilles Tendinosis", Acta Radiologica, 2002, 43, 198-206.
Tarr, "Manual Edman Sequencing System", Chapter 6, Methods of Protein Micro-Characterization Characterization A Practical Handbook, 1986, 155-194.
Tauro et al., "Arthroscopic Interval Slide in the Repair of Large Rotator Cuff Tears", Arthroscopy, 1999, 15(5), 527-530.
Youssef et al., "Glucocorticoid-Like Effects of Antihepatocarcinogen Rotenone are Mediated via Enhanced Serum Corticosterone Levels: Molecular Fitting and Receptor Activation Studies", J. Carcinogenesis, 2003, 2, 8 pages.
Zheng et al., Porcine Small Intestine Submucosa (SIS) Is Not an Acellular Collagenous Matrix and Contains Porcine DNA: Possible Implications in Human Implantation, Wiley InterScience, www.interscience.wiley.com, Feb. 2005, 7 pages.
Chen et al., "Autologous Tenocyte Therapy Using Porcine-Derived Bioscaffolds for Massive Rotator Cuff Defect in Rabbits," Tissue Engineering, Jul. 2007, vol. 13, No. 7, pp. 1479-1491.
Derwent Online Abstract Accession No. 2004-643139/63, B04 D16 (D22) & CN 1507926 A (No 9 Peoples Hospital Attached to Shanghai) Jun. 30, 2004 Abstract—"Tendon Tissue Engineered Seed Cell-Hypodermal Fibroblast", 7 pages.
Gauger et al., "A low-serum medium for tendon cells: effects of growth factors on tendon cell growth and collagen production", In Vitro Cellular and Developmental Biology, Jan. 1, 1985 vol. 21, No. 5, 291-296.
Kuroyanagi & Sato, "Prednisolone Glycyrrhizine Passive Transfer", Allergy, 1966, 15, 67-75.
Margaret Wan Nar Wong et al., "Glucocorticoids suppress proteoglycan production by human tenocytes", Acta Orthopaedica, Jan. 1, 2005, vol. 76, No. 6, 927-931.
Wang et al., "Autologous Tenocyte Implantation on Collagen Bioscaffolds Improve Healing of rotator Cuff Tendon Defects in a Rabbit Model," Abstract, Journal of Bone and Joint Surgery-British Volume, Oct. 24-29, 2004, vol. 87-B, Issue SUPP_III, 333.
Wei et al., "Use of Polyglycolic Acid Unwoven and Woven Fibers for Tendon Engineering in vitro," Key Engineering Materials, Jun. 2005, vols. 288-289, pp. 7-10, Abstract.
Willers et al., "Autologous Tenocyte Implantation for Massive Histological Assessment in the Rabbit," Online Abstract: http://www.anzors.org.au/abstracts2005/abstract34.html, Australian Rotator Cuff Defect: & New Zealand Orthopaedic Research Society: Listing of Abstracts, 2005, 2 pages.
Yilin et al., "Bridging Tendon Defects Using Autologous Tenocyte Engineered Tendon in a Hen Model," Plastic and Reconstructive Surgery, Oct. 2002, vol. 110, No. 5, pp. 1280-1289, Abstract.
Chrousos et al., "Glucocorticoid Therapy and Adrenal Suppression", EndoText [Internet], http://ncbi.nlm.nih.gov/books/NBK279156, Jan. 11, 2011, 45 pages.

* cited by examiner

| PCR Target | Product Size (bp) | Sequence of Primers (5' to 3') | Conditions (Annealing) |
|---|---|---|---|
| Rabbit Type I Collagen | 464 | Sense: CTCGCTCACCACCTTCTCTC | 60°C 40sec, 30 cycles |
| | | Antisense: TGTTCTGAGAGGCGTGATTG | |
| Rabbit Type III Collagen | 254 | Sense: ACCAACCTCTTCCTGAAGCC | 60°C 40sec, 30 cycles |
| | | Antisense: CACCATTGAGACATTTTGAA | |
| Rabbit EphA4 | 1205 | Sense: AGATGGTGAATGGCTGGTACC | 58°C 40sec, 35 cycles |
| | | Antisense: ATGATGCTGGCCTCACTCAGG | |
| Rabbit GAPDH | 293 | Sense: TCACCATCTTCCAGGAGCGA | 62°C 40sec, 30 cycles |
| | | Antisense: CACAATGCCGAAGTGGTCGT | |

| | Time Points | Control (mm) | ACI Maix™ (mm) | ACI Maix™ + Tenocytes (mm) | Restore™ (mm) | Restore™ + Tenocytes (mm) | Normal (mm) |
|---|---|---|---|---|---|---|---|
| Thickness | 4 week | 3.2±0.8 | 3.3±0.8 | 3.3±0.5 | 2.8±0.6 | 3.0±0.4 | 2.5±0.3 |
| | 8 week | 2.2±0.5 | 1.7±0.5 | 2.0±0.5 | 1.5±0.2 | 1.3±0.2 | |
| Width | 4 week | 7.0±0.2 | 6.9±0.3 | 6.4±0.2 | 6.7±0.5 | 6.8±0.5 | 6.6±0.5 |
| | 8 week | 6.7±0.3 | 6.9±0.3 | 6.8±0.4 | 6.9±0.3 | 6.8±0.3 | |
| Length | 4 week | 13.1±1.1 | 14.2±0.9 | 13.8±0.9 | 13.9±0.6 | 13.9±0.4 | 8.8±0.5 |
| | 8 week | 12.8±1.0 | 14.3±0.8 | 14.2±0.9 | 13.8±0.7 | 13.5±0.7 | |

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ctcgctcacc accttctctc                                                  20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
tgttctgaga ggcgtgattg                                              20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
accaacctct tcctgaagcc                                              20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
caccattgag acattttgaa                                              20

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
agatggtgaa tggctggtac c                                            21

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
atgatgctgg cctcactcag g                                            21

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
tcaccatctt ccaggagcga                                              20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
cacaatgccg aagtggtcgt                                              20

TENOCYTE CONTAINING BIOSCAFFOLDS AND TREATMENT USING THE SAME

CROSS REFERENCE TO RELATED APPLICATIONS

This application is a U.S. national stage application of International Application No. PCT/AU2008/000583, filed Apr. 24, 2008, which claims the benefit of Australian Patent Application No. 2008901451, filed Mar. 26, 2008 and Australian Patent Application 2007902168, filed Apr. 24, 2007, all three of which are incorporated herein by reference in their entirety.

FIELD

The present invention relates to methods for preparing bioscaffolds useful in the repair of tears. More specifically, the present invention relates to the repair of rotator cuff tears using bioscaffolds seeded with tenocytes.

INTRODUCTION

Rotator cuff tendon tear is a common presentation resulting from injuries sustained from overhead activities (Briner et al., (1997) *Sports Med.* 24(1):65-71). Numerous studies have described different techniques for tendon repair. These include suture techniques (Gerber et al., (1999) *J. Bone Joint Surg. Am.* 81(9):1281-90), tendon to bone fixation (Burkhart et al., (2000) *Arthroscopy.* 16(7):82-90), tendon mobilizing and sliding techniques for retracted tears (Tauro at al., (1999) *Arthroscopy.* 15(5):527-30) and use of various tissue or synthetic tendon grafts (Amstutz at al. (1976) *J. Biomed. Mater. Res.* 10(1):47-59).

While surgical repair usually achieves high levels of functional improvement and patient satisfaction in the early post-operative stage, there is significant morbidity associated with large and chronic tears (Hattrup, (1995) *J. Shoulder Elbow Surg.* 4(2):95-100). In addition, the success rate of revision surgery for failed rotator cuff repair is very low (Bigliani at al. (1992) *J. Bone Joint Surg. Am.* 74(10):1505-15). Consequently, there is a need in the art to develop better methods of treating rotator cuff tear.

In an attempt to improve surgical outcomes bioscaffolds and synthetic implants (see U.S. Pat. Nos. 4,668,233, 4,775, 380, 5,352,463, 4,902,508, and EP 0 223 370) have been proposed in the treatment of rotator cuff tear. These devices are intended to encourage the invasion of tissue on implantation, in the hope that the tissue ingrowth, together with the device, will confer improved wound healing and functional improvement to the patient. However, devices for the treatment of rotator cuff tear have generally failed to show successful long-term results with failure commonly occurring due to the invasion of non-functional fatty tissue, tenosynovitis, loosening or implant failure. Further, continuous loading of the device and abrasion against joint tissues causes wear, creep and fatigue of the device and ultimately the device fails.

As such, the augmentation of surgical repair with devices such as bioscaffolds in rotator cuff tears has not been shown to improve the clinical outcome of patients (Iannotti, (1994) *J. Am. Acad. Orthop. Surg.* 2(2):87-95). As such, the current methods are sub-optimal and there is a need to develop better treatments for the repair rotator cuff tear.

SUMMARY

The inventors have now developed a novel cell-based tissue engineering approach to the treatment of rotator cuff tear comprising the implantation of a bioscaffold that has been seeded with tenocytes which have been expanded in vitro.

Accordingly, in a first aspect the present invention provides a method for treating rotator cuff tear in a mammalian subject in need thereof comprising the steps of: (i) selectively expanding tenocytes in vitro in culture medium comprising insulin or a functional derivative and a glucocorticoid or a glucocorticoid-like molecule to produce a culture of expanded tenocytes; (ii) seeding a bioscaffold with said expanded tenocytes to produce a tenocyte seeded bioscaffold; and (iii) implanting said tenocyte seeded bioscaffold proximal to a rotator cuff tear.

In some embodiments, the tenocyte seeded bioscaffold is cultured in vitro for sufficient time to establish the tenocytes before implantation.

In some embodiments, the rotator cuff tear is a massive rotator cuff tear.

It will be appreciated that the tenocytes used in the methods and devices of the invention as described herein can be isolated from any tenocyte-containing tissue. In some embodiments the tissue is a tendon. The tendon may be from any anatomical site of an animal and may be a rotator cuff tendon, supraspinatus tendon, subcapularis tendon, pectroalis major tendon, peroneal tendon, achille's tendon, tibialis anterior tendon, anterior cruciate ligament, posterior cruciate ligament, hamstring tendon, lateral ligament, medial ligament, patella tendon, biceps tendon, and triceps tendon.

In some embodiments, the tenocyte containing tissue may be isolated from any mammalian animal including, but not limited to a sheep, a cow, a pig or a human. In other embodiments, the tenocyte containing tissue is isolated from a human. In still other embodiments the tenocyte containing tissue is isolated from the subject in need of treatment.

The isolated tenocytes are selectively expanded by in vitro culture in the presence of a culture medium comprising insulin or functional derivative. In some embodiments the culture medium comprises about 0.00005% to 0.1% w/v insulin or functional derivative. In other embodiments the culture medium comprises about 0.0001% to 0.001% w/v insulin or functional derivative. In still other embodiments the culture medium comprises about 0.0006% w/v insulin or functional derivative.

The culture medium may further comprise a glucocorticoid, such as a synthetic glucocorticoid, or a glucocorticoid-like molecule. In some embodiments the glucocorticoid is betamethasone. The culture medium may comprise about 0.00001% to 0.1% w/v glucocorticoid or a glucocorticoid-like molecule. In some embodiments the culture medium comprises about 0.0001% to 0.001% w/v glucocorticoid or a glucocorticoid-like molecule. In still other embodiments the culture medium comprises about 0.0002% w/v glucocorticoid or a glucocorticoid-like molecule.

In some embodiments, the culture of expanded tenocytes comprises at least 80% tenocytes and no more than 20% non-tenocyte cells. In other embodiments at least 90% of the cells in the culture are tenocytes. In still other embodiments at least 95% of the cells present in the selectively expanded tenocyte culture are tenocytes.

In some embodiments, the expanded tenocyte culture comprises cells, wherein at least 80% of said cells express one or more genes coding for the following: type I collagen, type III collagen, EphA4, scleraxis, Six1, COMP and/or Cbfa1.

In a second aspect, the present invention provides a method of treating massive rotator cuff tear in a human subject in need thereof comprising the steps of: (i) isolating tenocytes from tendon tissue taken from said subject; (ii) selectively expanding said tenocytes in vitro in a culture medium comprising about 0.0006% w/v insulin or functional derivative and about 0.0002% w/v glucocorticoid or a glucocorticoid-like molecule to produce a culture of expanded tenocytes comprising at least 80% tenocytes; (iii) seeding a bioscaffold with said expanded tenocytes and culturing said bioscaffold and tenocytes for no more than five days to produce a tenocyte seeded bioscaffold; and (iv) implanting said tenocyte seeded bioscaffold into the rotator cuff tear.

In a third aspect, the invention provides a bioscaffold comprising cells, wherein more than 800 of said cells are tenocytes. In some embodiments, the bioscaffold comprises at least 90%, 95% or 99% tenocyte cells.

The bioscaffold may comprise cells, wherein at least 80% of said cells express one or more genes coding for the following: type I collagen, type III collagen, EphA4, scleraxis, Six1, COMP and/or Cbfa1.

The bioscaffold may comprise a matrix, a membrane, a microbead, a fleece, a thread, or a gel, and/or mixtures thereof. In some embodiments the bioscaffold comprises a type I/III collagen matrix (ACI Matrix™) or small intestinal submucosa (Vitrogen™).

BRIEF DESCRIPTION OF THE FIGURES

FIG. 15: Working conditions for, and primer sequences of, rabbit type I collagen sense primer (SEQ ID NO:1), rabbit type I collagen antisense primer (SEQ ID NO:2), rabbit type III collagen sense primer (SEQ ID NO:3), rabbit type III collagen antisense primer (SEQ ID NO:4), rabbit EphA4 sense primer (SEQ ID NO:5), rabbit EphA4 antisense primer (SEQ ID NO:6), rabbit GAPDH sense primer (SEQ ID NO:7), and rabbit GAPDH antisense primer (SEQ ID NO:8).

FIG. 16: Geometric measurement: Normal thickness, width and length were measured from fifty normal rabbit rotator cuff tendon harvested from unoperated shoulder. All measurements were performed under slack condition at room temperature.

DETAILED DESCRIPTION OF THE PREFERRED EMBODIMENTS

Figure 1:
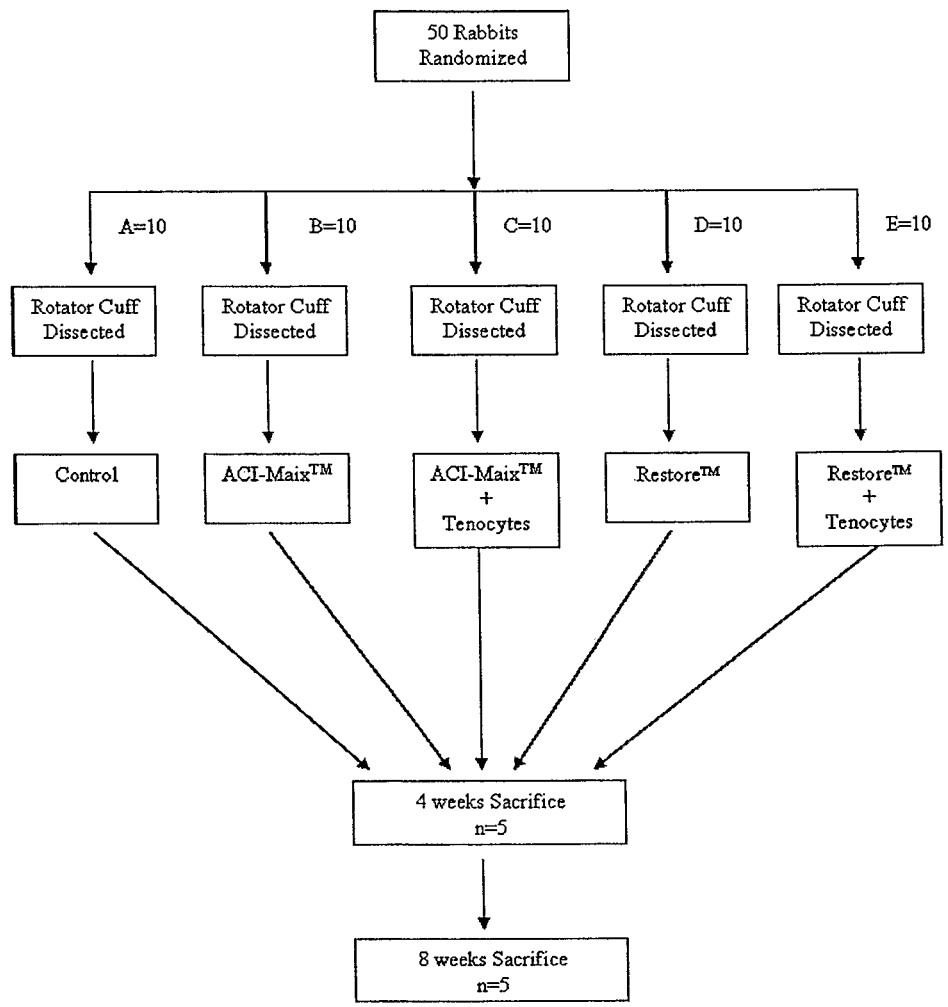
FIG. 1: Experimental design of animal study.

Before describing the present invention in detail, it is to be understood that this invention is not limited to particularly exemplified methods and may, of course, vary. It is also to be understood that the terminology used herein is for the purpose of describing particular embodiments of the invention only, and is not intended to be limiting which will be limited only by the appended claims.

All publications, patents and patent applications cited herein, whether supra or infra, are hereby incorporated by reference in their entirety. However, publications mentioned herein are cited for the purpose of describing and disclosing the protocols and reagents which are reported in the publications and which might be used in connection with the invention. Nothing herein is to be construed as an admission that the invention is not entitled to antedate such disclosure by virtue of prior invention.

The practice of the present invention will employ, unless otherwise indicated, conventional techniques of cell culture, cell biology and orthopedic surgery, which are within the skill of the art. Such techniques are described in the literature. See, for example, Coligan et al., 1999 "Current protocols in Protein Science" Volume I and II (John Wiley & Sons Inc.); Ross et al., 1995 "Histology: Text and Atlas", $3^{rd}$ Ed., (Williams & Wilkins); Kruse & Patterson (eds.) 1977 "Tissue Culture" (Academic Press); Canale (ed.) 2003 "Campbell's Operative Orthopaedics" $10^{th}$ ed. (St. Louis, Mo.: MD Consult LLC); and Alberts et al. 2000 "Molecular Biology of the Cell" (Garland Science).

It must be noted that as used herein and in the appended claims, the singular forms "a," "an," and "the" include plural reference unless the context clearly dictates otherwise. Thus, for example, a reference to "a cell" includes a plurality of such cells, and a reference to "an agent" is a reference to one or more agents, and so forth. Unless defined otherwise, all technical and scientific terms used herein have the same meanings as commonly understood by one of ordinary skill in the art to which this invention belongs.

Although any materials and methods similar or equivalent to those described herein can be used to practice or test the present invention, the preferred materials and methods are now described.

In some embodiments, the present invention is directed towards a method for treating rotator cuff tear.

The terms "treating" or "treatment" or grammatical equivalents thereof are used herein to cover the treatment of a rotator cuff tear in a mammalian subject, preferably a human, and includes: (a) relieving or ameliorating the symptoms of a rotator cuff tear, i.e., cause regression of the symptoms of a rotator cuff tear; or (b) preventing or inhibiting rotator cuff tear from re-occurring in a subject that may be predisposed to rotator cuff tear, but has not yet been diagnosed as having it, e.g. a person who has previously been treated for rotator cuff tear. The effect of the treatment may be therapeutic in terms of a partial or complete cure of a rotator cuff tear or prophylactic in terms of completely or partially preventing the re-occurrence of rotator cuff tear.

The rotator cuff refers to the group of muscles and their tendons that act to stabilize the shoulder. The rotator cuff muscles are a group of four muscles that surround the shoulder (supraspinatus, infraspinatus, teres minor and subscapularis). The four rotator cuff muscle tendons combine to form a broad, conjoined tendon, called the rotator cuff tendon, and insert onto the bone of the humeral head in the shoulder.

The term "rotator cuff tear(s)" refers to a tear of one, or more, of the four tendons of the rotator cuff muscles or the conjoined tendon of the rotator cuff. Tears of the rotator cuff tendon may be partial thickness tears, full thickness tears or full thickness tears with complete detachment of the tendons from bone. Partial thickness tears refer to fraying of an intact tendon. Full thickness tears refer to wounds that persist through the entire tendon. These may vary in size from very small or pin-point to very large involving the majority of the tendon. Full thickness tears may also involve complete detachment of the tendon(s) from the humeral head.

In some embodiments, the rotator cuff tear is a massive rotator cuff tear.

The term "massive rotator cuff tear" refers to tears of more than about 5 cm and involves more than one tendon.

It will be appreciated that most mammalian animals comprise tendons and that all these tendons comprise collagen fibres embedded in a glycoprotein-rich matrix. Thus, in the present specification the term "mammalian subject" refers to any mammal, such as a human or mammals of economical importance and/or social importance to humans, for instance, carnivores other than humans (such as cats and dogs). Also provided for is the repair of rotator cuff injury in livestock, including, but not limited to, domesticated swine (pigs and hogs), ruminants, horses, and the like. The term does not denote a particular age. Thus, both adult and newborn subjects are intended to be covered.

In some embodiments, a first step involves the isolation of a population of tenocytes from a source. The term "tenocyte" as used herein refers to the spindle-shaped, fibroblast-like cells that are found in tendons of all mammals. Tenocytes typically have elongated nuclei and thin cytoplasm and are often found sitting on collagen fibres in tendons. Tenocytes can often be identified on the basis that they produce collagen type I and express the marker "scleraxis". Accordingly, in some aspects the tenocyte cells of the invention are scleraxis expressing cells or cells capable of expressing collagen type I or scleraxis.

The term "source" as used herein refers to any tenocyte-containing tissue in any mammal. In some embodiments, the tenocyte-containing tissue is a tendon. A tendon is the tissue which connects muscle to bone in a mammal. The tendon may be from any anatomical site of an mammal and may be a rotator cuff tendon, supraspinatus tendon, subcapularis tendon, pectroalis major tendon, peroneal tendon, achille's tendon, tibialis anterior tendon, anterior cruciate ligament, posterior cruciate ligament, hamstring tendon, lateral ligament, medial ligament, patella tendon, biceps tendon, and triceps tendon.

Tenocyte cells may be isolated from a source in a variety of ways, all which are known to one skilled in the art. In some embodiments, tenocyte cells can be isolated from a biopsy material by conventional methods. As described in more detail below, in some embodiments, tenocytes are isolated by enzymatic digestion.

In some embodiments, the tenocyte-containing tissue may be isolated from any mammalian animal including, but not limited to a sheep, a cow, a pig or a human. In other embodiments, the tenocyte-containing tissue is isolated from a human.

In some embodiments, the tenocyte-containing tissue is "autologous", i.e. isolated from the body of the subject in need of treatment for rotator cuff tear. For example, a mammalian subject with a rotator cuff tear can have a biopsy taken from any tendon in their body. Such tendons include, but are not limited to, tendon of flexor carpi radialis and the calcaneus tendon.

Tenocyte cells may be obtained from biopsy material by appropriate treatment of the tissue that is to serve as the source of the tenocyte cells. Techniques for treatment of tissue to obtain tenocyte cells are known to those skilled in the art see, for example, Freshney "Culture of Animal Cells. A Manual of Basic Technique" $2^{nd}$ ed. (A. R. Liss Inc.). For example, the tissue or organ can be mechanically disrupted and/or treated with digestive enzymes or chelating agents to weaken the interactions between cells making it possible to obtain a suspension of individual cells. Typically the method will include a combination of mechanical disruption, enzyme treatment and chelating agents. In one technique the tissue is minced and treated simultaneously or subsequently with any of a number of digestive enzymes either alone or in combination. Examples of enzymes useful in dissociating cells include, but are not limited to, trypsin, chymotrypsin, collagenase, elastase, hyaluronidase, DNase, pronase, dispase, and the like. In some embodiments, enzyme compositions containing an aqueous mixture of collagenase having an activity of about 43 nkat/ml to about 51 nkat/ml, and chymopapain having an activity of about 0.22 nkat/ml to about 0.44 nkat/ml are used for dissociating cells, such as described in U.S. Pat. No. 5,422,261. Mechanical disruption can also be accomplished by, for example, the use of blenders, sieves, homogenizers, pressure cells, and the like.

The resulting suspension of cells and cell clusters can be further divided into populations of substantially homogenous cell types. This can be accomplished using standard techniques for cell separation including, for example, positive selection methods (e.g., clonal expansion and selection of specific cell types), negative selection (e.g., lysis of unwanted cells), separation based upon specific gravity in a density solution, differential adherence properties of the cells in the mixed population, fluorescent activated cell sorting (FACS), and the like. Other methods of selection and separation are known in the art see, for example Freshney "Culture of Animal Cells. A Manual of Basic Technique" $2^{nd}$ ed. (A. R. Liss Inc.).

In some embodiments, tendon tissues, which have been isolated by biopsy, are washed, dissected and digested to form explants which can be grown in cell culture to yield free tenocytes. In some embodiments, the biopsy tissue is subjected to enzymatic digestion and/or subjected to agents such as ethylenediaminetetraacetic acid (EDTA) that bind or chelates $Ca^{2+}$ on which cell-cell adhesion depends. Examples of enzymes suitable for use include one or more of collagenase, trypsin, and proteases.

In some embodiments, minced tendon tissue of no larger than 1 mm is incubated in the presence of about 2.5% w/v trypsin and about 5.5% w/v collagenase in standard tissue culture medium without phenol red for at least 3 hours at about 37° C. in about 5% $CO_2$.

In some embodiments, after enzymatic digestion, the tenocytes are recovered from the biopsy material through centrifugation of the biopsy solution, and washing the resulting pellet with cell growth medium. Alternatively, the tenocytes may be recovered from the biopsy solution by filtration through, for example, a mesh such as a sterile 150 micron nylon mesh. Another approach is based on the tendency of some cell types to adhere strongly to plastic or glass, which allows them to be separated from components of a tendon which do not adhere as strongly. Alternatively, the cells may be separated from other components of the tendon using antibodies that specifically bind to the cell, for example using antibodies conjugated to a matrix or coupled to a fluorescent dye which can then be separated by fluorescent-activated cell sorting (FACS). In some embodiments, the tenocytes are isolated by filtration of the biopsy solution through a 0.22 μm filter to remove matrix debris and the filtrate centrifuged to form a cell pellet. The pellet is then washed in cell growth medium.

The isolated tenocytes are selectively expanded in vitro. The term "selectively expanded" as used herein refers to culturing the isolated tenocytes in such a way as to grow and increase the number of tenocyte cells to the detriment of other cell types.

In some embodiments, the isolated tenocytes are expanded in vitro in a culture medium comprising insulin or functional derivative. Insulin is a hormone which, in its naturally-occurring form, is produced by the pancreas. However, the insulin used in culture medium for the selective expansion of tenocytes may be synthetic, such as recombinant insulin, or naturally occurring.

A "functional derivative" of insulin is a molecule such as those described by Chan et al., 2000, "Insulin-through the ages: Phylogeny of a growth promoting and metabolic regulatory hormone" (American Zoologist, 40(2):213-222) having the activity of insulin, namely, the ability to culture tenocytes and includes biologically active fragments, variants, and derivatives of insulin.

In some embodiments, a "functional derivative" of insulin or a fragment or variant thereof has one or several amino acid residues substituted by naturally occurring or synthetic amino acid homologues of the 20 standard amino acids. Examples of such homologues are 4-hydroxyproline, 5-hydroxylysine, 3-methylhistidine, homoserine, ornithine, beta-alanine and 4-aminobutanoic acid, beta-alanine, norleucine, norvaline, hydroxyproline, thyroxine, gamma-amino butyric acid, homoserine, citrulline, and the like.

A functional derivative of insulin can be prepared using polyethylene glycol (PEG) according to the method of Sehon and co-workers (Wie et al., supra) to produce an insulin molecule conjugated with PEG. In addition, PEG can be added during chemical synthesis of insulin. Other methods of preparing a derivative of insulin or a fragment thereof include reduction/alkylation (Tarr, Methods of Protein Micro-characterisation, J. E. Silver ed., Humana Press, Clifton N.J. 155-194 (1986)); acylation (Tarr, supra); chemical coupling to an appropriate carrier (Mishell and Shiigi, eds, Selected Methods in Cellular Immunology, W H Freeman, San Francisco, Calif. (1980), U.S. Pat. No. 4,939,239; or mild formalin treatment (Marsh, 1971, *Int. Arch. of Allergy and Appl. Immunol.*, 41:199-215).

It should be noted that the term "functional derivative" does not include molecules such as insulin-like growth factor I or II.

The insulin or functional derivative may be incorporated into the culture medium prior to adding the tenocyte cells to be cultured. Alternatively, the insulin or functional derivative may be added to the medium throughout the culture, for example, by culturing the cells in the presence of a cell feeder layer, such as beta cells, which secrete insulin or a functional derivative.

As used herein a "fragment" is a portion of the insulin protein which retains the function of insulin and in particular, the ability to support the growth of tenocyte cells in culture. A fragment of insulin can be at least about 10 amino acid residues in length, preferably about 10-16 amino acid residues in length, and more preferably about 10-20 amino acid residues in length.

A "variant" of insulin is an insulin molecule that has one or more substitutions such that the secondary conformation thereof remains unchanged. Examples of such conservative substitutions include amino acids having substantially the same hydrophobicity, size and charge as the original amino acid residue. Such substitutions are generally well known to those skilled in the art of protein or peptide chemistry. For example, conservative substitutions include proline for glycine and vice versa; alanine or valine for glycine and vice versa; isoleucine for leucine and vice versa; histidine for lysine and vice versa; threonine for cysteine and vice versa; glutamine for asparagine and vice versa; and arginine for glutamate and vice versa.

Another example of a variant of insulin is one in which the cysteine residues have been substituted to minimise dimerisation via disulfide linkages. Preferably the cysteine residues are substituted with alanine, serine, threonine, leucine or glutamic acid residues. In addition, amino acid side chains of insulin or fragment or derivative thereof can be chemically modified. Another modification is cyclisation of the insulin.

In some embodiments the culture medium comprises about 0.00005% to 0.1% w/v insulin or functional derivative. In other embodiments the culture medium comprises about 0.0001% to 0.001% w/v insulin or functional derivative. In still other embodiments the culture medium comprises about 0.0006% w/v insulin or functional derivative.

The culture medium may further comprise a glucocorticoid, such as a synthetic glucocorticoid, or a glucocorticoid-like molecule. Glucocorticoids are a class of steroid hormones characterised by an ability to bind to the cortisol receptor and trigger similar effects, such as affecting metabolism or anti-inflammatory or immunosuppressive effects. Glucocorticoids may be naturally-occurring (hormones) or synthetic (drugs).

Examples of synthetic glucocorticoids suitable for use in culture medium for the selective expansion of tenocytes include hydrocortisone, cortisone acetate, predisone, prednisolone, methylprednisolone, dexamethasone, betamethasone, triamcinolone, beclometasone, fludrocortisones acetate, deoxycorticosterone acetate (DOCA), and aldosterone.

A "glucocorticoid-like" molecule may be any molecule having an activity of a glucocorticoid, namely the ability to culture tenocytes. Examples of glucocorticoid-like molecules suitable for use in the invention include the antihepatocarcinogen, Rotenone (Youssef et al., 2003, *J. Carcinogenesis* 2:2), Rifampcin (Calleja et al., 1998, *Nat. Med.*, 4:92-96), Glycyrrhizin (a component of licorice) (Kuroyanagi & Sato, 1966, *Allergy*, 15:67-75), and Withanolides (from the herb *Withanthia somnifera*) (Grandhi et al., 1994, *J. Ethnopharmacol.*, 44:131-135).

In some embodiments the glucocorticoid is beta-methasone. Beta-methasone is a synthetic glucocorticoid having the formula $C_{22}H_{29}FO_5$.

The culture medium may comprise about 0.00001% to 0.1% w/v glucocorticoid or a glucocorticoid-like molecule. In some embodiments the culture medium comprises about 0.0001% to 0.001% w/v glucocorticoid or a glucocorticoid-like molecule. In still other embodiments the culture medium comprises about 0.0002% w/v glucocorticoid or a glucocorticoid-like molecule.

In some embodiments, the isolated tenocytes are cultured for about 3 days to about five weeks, at about 37° C. in about 5% $CO_2$ atmosphere. The time period for cell culturing can, of course, vary.

The resultant culture of "expanded tenocytes" can be termed a substantially pure culture of tenocytes. The term "substantially pure" as used herein means that the predominant cells in the culture are tenocytes and other contaminating cells such as fibroblasts, chondrocytes and the like are of a lesser number. In some embodiments, the expanded tenocytes are at least 80% tenocytes and no more than 20% non-tenocyte cells. In other embodiments at least 90% of the cells are tenocytes. In still other embodiments at least 95% of the cells present in the expanded tenocyte culture are tenocytes.

In some embodiments, the expanded tenocyte culture comprises cells, wherein at least 80% of said cells express one or more genes coding for the following: type I collagen, type III collagen, EphA4, scleraxis, Six1, COMP and/or Cbfa1.

The selectively expanded tenocytes can be seeded onto a bioscaffold. The term "bioscaffold" refers to any matrix or scaffold that is suitable for tenocyte or cell adherence with or without an adhesive. By way of example and not limitation, the bioscaffold can be in the form of a membrane, microbead, fleece, thread, or gel, and/or mixtures thereof. The bioscaffold can be made out of any material that has the physical or mechanical attributes required for implantation, such as acting as a haemostatic barrier. A haemostatic barrier inhibits penetration of adjunct cells and tissue into the treated defect area.

In some embodiments the bioscaffold is made of a semi-permeable material which may include cross-linked or uncross-linked collagen, preferably type I in combination with type III, or type II. The bioscaffold may also include polypeptides or proteins obtained from natural sources or by synthesis, such as hyaluronic acid, small intestine submucosa peritoneum, pericardium, polylactic acids and related acids, blood (i.e., which is a circulating tissue including a fluid portion (plasma) with suspended formed elements (red blood cells, white blood cells, platelets), or other material which is bioresorbable. Bioabsorbable polymers, such as elastin, fibrin, laminin and fibronectin are also useful in the present invention. Support matrix or scaffold materials as described in US Publication No. 20020173806, herein incorporated by reference in its entirety, are also useful in the present invention.

The bioscaffold is preferably initially (i.e., before contact with the cells to be transplanted) free of intact cells and is resorbable within the mammalian subject. The bioscaffold may have one or several surfaces, such as a porous surface, a dense surface, or a combination of both. The bioscaffold may also include semi-permeable, impermeable, or fully permeable surfaces. Support matrices having a porous surface are described, for example, in U.S. Pat. No. 6,569,172, which is incorporated herein by reference in its entirety.

The bioscaffold may be autologous or allogeneic. In some embodiments, a suitable autologous support matrix is formed from blood, as exemplified in U.S. Pat. No. 6,368,298, issued to Berretta, et al. on Apr. 9, 2002, herein incorporated by reference in its entirety.

A suitable bioscaffold may be a solid, semi-solid, gel, or gel-like scaffold characterized by being able to hold a stable form for a period of time to enable the adherence and/or growth of cells thereon, both before transplant and after transplant, and to provide a system similar to the natural environment of the cells to optimize cell growth. Examples of suitable support matrices are disclosed in US Publication No. 20020173806, which is hereby incorporated by reference in its entirety.

Additional examples of suitable bioscaffold for growth of tenocytes include Vitrogen™, a collagen-containing solution which gels to form a cell-populated matrix, and the connective-tissue scaffolds of Hwang (US patent application no. 20040267362), Kladaki at al (US patent application no. 20050177249), Giannetti (US patent application no. 20040037812) and Binette et al (US patent application no. 20040078077); all of which are incorporated herein by reference.

The bioscaffold can be cut or formed into any regular or irregular shape. In some embodiments, the bioscaffold can be cut to correspond to the shape of the tear. The bioscaffold can be flat, round and/or cylindrical in shape. The shape of the bioscaffold can also be moulded to fit the shape of a particular tear. If the bioscaffold is a fibrous material, or has the characteristics of a fibre, the support matrix can be woven into a desired shape. Alternatively, the bioscaffold can be a gel, gel-like, or non-woven material.

In some embodiments the bioscaffold is comprised of porcine-derived type I/III collagen, for example, ACI Matrix™. In other embodiments the bioscaffold is comprised of small intestinal submucosa, for example Restore™.

The term "seeded" refers to bringing the tenocyte cells into contact with a bioscaffold for a sufficient time prior to transplantation such that they adhere (with or without an adhesive) to the bioscaffold. In some embodiments the cells are cultured with the bioscaffold overnight or more than a week. In some embodiments, the selectively expanded tenocytes are cultured in vitro with the bioscaffold for about five days before use.

In some embodiments, uniform seeding is preferable. It is believed that the number of tenocyte cells seeded does not limit the final tissue produced; however optimal seeding may increase the rate of generation. Optimal seeding amounts will depend on the specific culture conditions. In some embodiments, the bioscaffold is seeded with about 0.05 to about 5 times the physiological cell density of a native tissue type, i.e., in tendon. In another embodiment, the cell density can be less than about $1\times10^6$ to $1\times10^7$ cells, or more, per cm$^2$, typically about $4\times10^6$ cells per cm$^2$. In some embodiments, the bioscaffold is seeded with about $3.5\times10^6$ selectively expanded tenocytes per cm$^2$.

It will be appreciated that the bioscaffold seeded with selectively expanded tenocytes can be packaged and sold as a device. Accordingly, in some embodiments, the present invention provides a bioscaffold seeded with tenocytes. The device packaging might comprise a plastic plate sealed with a sheet of sterile adhesive film, as exemplified in U.S. Pat. No. 5,842,573, herein incorporated by reference.

In some embodiments, the device is implanted at a site proximal to the rotator cuff tear.

The terms "implanted" or "implantation" or grammatical equivalents thereof are used herein to cover any act that introduces a bioscaffold containing tenocytes into the rotator cuff of a subject.

The term "proximal" refers to a site within the rotator cuff such that treatment at that site will cause regression of the symptoms of the rotator cuff tear.

In some embodiments the tenocyte seeded bioscaffold is implanted into the tear cells facing down onto the tear. In some embodiments, a covering patch serves to cover the defect to further prevent infiltration of undesired materials, such as fibroblasts or macrophages, from the surrounding environment. In some embodiments, the covering patch may be any of the support matrices described herein, and/or can include collagen (type I/III), hyaluronic acid, fibrin and polylactic acid. Preferably, the covering patch is cell-free and resorbable, and may be semi-permeable.

The tenocyte seeded bioscaffold may be secured in place by any conventional means known to those skilled in the art, e.g. suturing, suture anchors, bone fixation devices and bone screws. In some embodiments, the tenocyte seeded bioscaffold is sutured into position.

The present invention also provides a bioscaffold comprising cells, wherein more than 80% of said cells are tenocytes. In some embodiments, at least 90% of the cells in the bioscaffold are tenocytes. In still other embodiments at least 95% of the cells present in the bioscaffold are tenocytes.

Alternatively, the bioscaffold may comprise cells, wherein at least 80% of said cells express one or more genes coding for the following: type I collagen, type III collagen, EphA4, scleraxis, Six1, COMP and/or Cbfa1.

The invention will now be further described by way of reference only to the following non-limiting examples. It should be understood, however, that the examples following are illustrative only, and should not be taken in any way as a restriction on the generality of the invention described above. In particular, while the invention is described in detail in relation to massive rotator cuff tear, it will be clearly understood that the findings herein are not limited to massive rotator cuff tear per se, but also encompasses the lesser rotator cuff tendon injuries described supra.

Example 1

Animals and Bioscaffolds

Fifty Albino New Zealand White (*Oryctolagus cuniculus*) rabbits between 12 to 20 weeks old with body weight between 3-5 kg were used in this study. All rabbits were bred from an out bred rabbit colony maintained in the animal house facility of the University of Western Australia (Nedlands, Australia). Rabbits were fed ad libitum with rabbit/guinea pig pellets, hay, and provided water ad libitum. Rabbits were held in cages measuring 1.5 m wide, 0.75 m long, and 0.75 m high, with grid floors to prevent pod dermatitis. All operative procedures and cage activities were conducted under strict guidelines detailed by the National Health and Medical Research Council (NHMRC, Can berra, Australia).

Porcine-derived type I/III collagen bioscaffold (ACI Maix™) was supplied and manufactured by Matricel (Herzogenrath, Germany). The collagen bioscaffold is a white complex with two different sides: the rough side and the smooth side. The rough side appears as cross linking fibres with pore size around 200 μm while the smooth side shows a compact arrangement of fibres (Willers et al. 2005). The mechanical property at breaking point is about 14.6+2.4N/mm$^2$ (Chen J. M. Unpublished data from previous study). A bioscaffold of small intestinal submucosa (Restore™) was manufactured by Depuy (USA). The small intestinal submucosa (SIS) bioscaffold is a 1 mm thick, highly compacted material with semitransparent appearance which consists of 10 sheets of individual small intestinal submucosas laminated together by vacuum drying. Both sides of the bioscaffold are very smooth (Zheng et al. 2005). The highly compacted structure of the SIS bioscaffold endues it with a very strong tensile strength around 75.6+6.3N/mm$^2$ at breaking point (Chen J. M. Unpublished data from previous study).

Example 2

Experimental Design

The fifty rabbits were randomly allocated into five groups of ten (FIG. 1). The left rotator cuffs were fully dissected and reconstructed by one of the five following methods: (1) Group A (Control treatment): The tendon excised during defect creation was in situ reimplanted into the defect immediately and sutured to the bone trough using 5-0 absorbable sutures; (2) Group B (ACI-Maix™): The defect was repaired by suturing ACI-Maix™ collagen bioscaffold as an interposition graft to the native tendon and bone trough borders; (3) Group C (ACI-Maix™ with autologous tenocytes): The cell-bioscaffold composite was used to repair the cuff defect in an identical manner to Group B; (4) Group D (Restore™): The cuff defect was repaired in an identical manner to Group B, but using Restore™ as an interposition graft; and (5) Group E (Restore™ with autologous tenocytes): The tenocytes seeded Restore™ composite was used to repair the cuff defect in an identical manner to Group C. In each group, five of the ten rabbits were euthanized at four weeks, and the others euthanized at eight weeks.

All statistical data are expressed as mean±standard deviation and compared by ANOVA using statistic software SPSS (SPSS inc. USA). P-values less than 0.05 were considered significant.

Example 3

Harvest and Culture of Tenocytes

Figure 2:
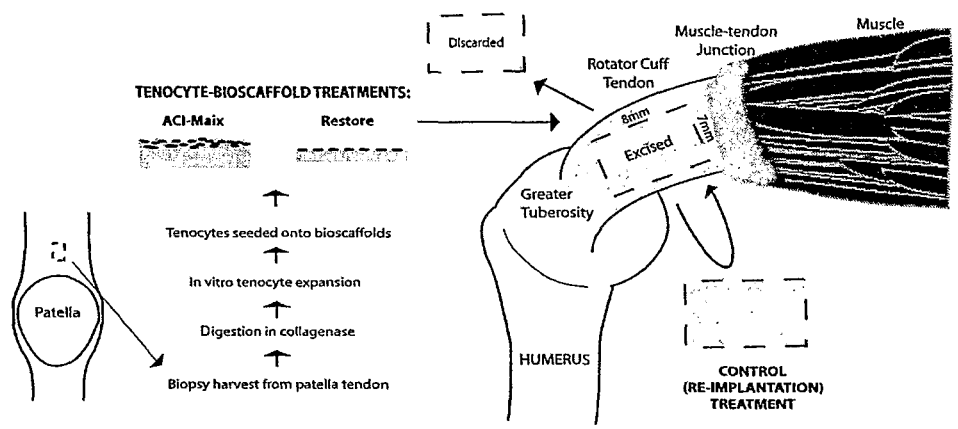
FIG. 2: Model of massive rotator cuff tear in the rabbit.

As shown in FIG. 2 tendon tissue of 3 mm diameter was obtained by biopsy punch from the rabbit patellar tendon and was washed in DMEM F-12 medium (GIBCO, Invitrogen, USA) supplemented with 10% fetal bovine serum (FBS), 100 µl/ml penicillin and 100 µg/ml streptomycin (hereafter medium refers to the same contents). The tendon tissue was then dissected into 0.5 mm of diameter and digested with collagenase (100 UI/ml Gibco, Invitrogen, USA) over night at 37° C. After the digestion, the solution was filter through a 0.22 µm filter to remove matrix debris and the cells released from tissue were centrifuged into pellet at 2000 rpm for 8 min. Supernatant containing enzymes were discarded and the pellet was resuspend in new medium. This washing process was repeated three times.

The cell pellet of resultant tenocytes was then resuspended in 5 ml of medium and placed into a culture flask at density between $10^3$ to $10^4$ cells/ml containing culture medium. This culture medium contains Dulbecco's Modified Eagle Medium (DMEM) (Invitrogen), 15% v/v fetal bovine serum, 0.0006% w/v insulin, 0.0002% w/v betamethasone, 0.5% w/v penicillin, 0.5% w/v streptomycin, and 0.6% L-proline at pH 7.0. The cells are then incubated under 5% $CO_2$ at 37° C. The culture medium should be changed every third day for 3 to 5 weeks until cells reach the maximum cell numbers at the fifth passage, typically $20 \times 10^7$ cells. For implantation, tenocytes of passage two were loaded onto either ACI Maix™ (rough side) or Restore™ bioscaffold at a density around $3.5 \times 10^6 /cm^2$ and cultured for up to 5 days to formulate cell seeded bioscaffolds prior to implantation.

Example 4

Comparison of in vivo and in vitro mRNA Expression in Tenocytes

To confirm whether tenocytes maintained their phenotype during cultivation, the expression of type I/III collagen and EphA4 mRNA was examined. Total RNA samples were extracted from both tendon tissue and in vitro cultured tenocytes using RNeasy Mini Kit (QIAGEN Australia). RNA was reverse-transcribed into cDNA using RETROscript™ First-strand Synthesis Kit (Ambion USA). Semi-quantitative RT-PCR was performed to generate and amplify type I/III collagen and EphA4 cDNA. The final PCR products were analysed by electrophoresis on 1.2% agarose gel and visualized by UV transilluminator (IBI) and Polaroid film. The experiment was repeated four times to ensure the integrity of the result. The PCR amplification was performed according to the conditions listed in FIG. 15.

Example 5

Immunostaining for Type I Collagen Protein on Tenocytes In Vitro Culture

To confirm whether tenocytes maintain their ability to produce type I collagen in culture, immunostaining was conducted in the following sequences: place culture passage two tenocytes in a 6-well plate; at 50% confluence fix with 4% paraformaldehyde for 10 min at room temperature; block endogenous peroxidase with 3% $H_2O_2$ for 5 minutes; rinse in 3 changes of Tris buffer saline (TBS); permeabilize cells with 0.1% TritonX100 for 5 min; wash twice with 0.2% bovine serum albumin (BSA Sigma, USA)/phosphate buffered saline (PBS); incubated with either collagen I (1:3000 abcam, cat: 106017, UK) primer antibody dilute in 0.2% BSA/PBS for 1 hr at room temperature (negative control treated with PBS at this step); wash 4 times with 0.2% BSA/PBS, 4 times PBS and 4 times 0.2% BSA/PBS; incubated with second antibody using LSAB system (Dako, cat: K0675 Denmark); repeat the washing procedure; visualized with DAB kit (Dako, cat: K3468 Denmark) staining the protein brown.

Example 6

Morphological Characterization of Tenocyte-Seeded Bioscaffolds

To determine the behaviours of tenocytes on the bioscaffolds, the morphology of tenocyte-seeded bioscaffolds on days 1, 3 and 5 of culture was studied by scanning electron microscopy (SEM). Samples were fixed in 2.5% glutaraldehyde (TAAB, Reading, UK) for 7 days at room temperature then treated with tannic acid. Samples were rinsed in 0.2M cacodylate buffer; post-fixed in 1% osmium tetroxide in cacodylate buffer for 60 min at room temperature; washed in 3 changes of cacodylate buffer; placed in 1% tannic acid in 0.05 cacodylate buffer for 60 min at room temperature; washed in saline solution; stained 60 min in 0.5% uranyl acetate in double-distilled water; rinsed in saline solution; placed in 25%, 50%, 70%, 95% and absolute ethanol sequentially for 30 min each at room temperature; and then washed twice in super dry ethanol for 30 min each at room temperature. After critical point drying, samples were mounted and viewed using a Phillips XL30 scanning electron microscope.

Example 7

Operative Techniques

Fifty rabbits were anaesthetized by intramuscular injection of Ketamine (Parke-Davis, Auckland, NZ) and Xylazine (Troy Laboratories Australia). A longitudinal incision over the left shoulder (The right shoulder was not operated.) was made and surgical exposure of the rotator cuff tendon was achieved by releasing a portion of the trapezius and deltoid muscles from the acromion. The whole rotator cuff tendon was fully excised from the tendon-bone insertion to the muscle-tendon junction creating a rectangle defect of approximate 7×8 mm$^2$ in area (FIG. 2). Using a dental burr, a bone trough 10 mm long, 2 mm wide, and 2 mm deep was prepared at the greater tuberosity perpendicular to the tendon fibre direction. Two small drill holes, 0.5 mm in diameter, were made from the lateral aspect of the humerus into the bony trough. Then the defect was repaired using the method correspond to its group. Following tendon reconstruction, the wound was closed in layers and dressed, but the limb was not splinted.

Example 8

Sample Harvest and Geometric Evaluation

At both 4 and 8 weeks, rabbits were anaesthetized and sacrificed by intravenous injection of pentobarbitone. The humerus head, cuff tendon and part of the muscle were harvested from both shoulders (operated and unoperated). Under slack condition, the length and width of both the operated and unoperated tendon were measured with a vernier caliper and the thickness was measured with a micrometer. Samples were then fixed in 4% paraformaldehyde. After fixation, the specimens were decalcified with 10% formic acid, dehydrated, paraffin-embedded, cut to 5 µm sections and stained with hematoxylin and eosin and Alcian Blue.

Example 9

Histology Examination

Inflammation response to the implants was evaluated by the inflammation rate which was interpreted as the percentage area of the repair tendon occupied by inflammatory cells. The whole tendon area and areas occupied by inflammatory cells were measured using graphical software Image Pro Plus 4.5 (Media cybernetics, USA). General histological examination was performed with hematoxylin and eosin and Alcian Blue staining. Eight parameters were semi-quantitatively assessed (Movin et al. 1997; Shalabi et al. 2002): (1) fibre structure, (2) fibre arrangement, (3) rounding of the nuclei, (4) inflammation, (5) increased vascularity, (6) bone-tendon junction, (7) biocompatibility (absorption rate of the implanted material), and (8) glycosaminoglycan content (the intensity of blue colour on Alcian Blue section). Zero to three points were allotted to each of these variables, with 0 being normal and 3 being maximally abnormal. Therefore, a perfectly normal tendon would have a score 0, and a maximally abnormal tendon would score 24.

The inflammation parameter was converted from the inflammation rate, which less than 10% scored 0, 10-20% scored 1, 20-30% scored 2, and more than 30% inflammatory cell infiltrate scored 3. The interpretation of bone-tendon junction was based on bone trough formation. If the bone trough presented typical tendon junction histology consisting of 4 zones, (cortical bone, mineralized fibrocartilage, fibrocartilage and tendon) it scored 0. The absence of one of these zones resulted in a score increase of 1, and a junction completely dissociated scored 3. This scoring system is a modification of Likert's grading (Movin et al. 1997; Shalabi et al. 2002).

Example 10

Immunostaining of Type I Collagen on Repair Tendon

To determine the ratio of cells that synthesized type I collagen protein, immunostaining was performed in following sequence: after dewaxing and rehydration, slides were digested with 0.1% trypsin for 20 min to retrieve the antigen; wash with water; blocked with endogenous peroxidase with 3% $H_2O_2$ for 5 min; washed with TBS three times for 5 min each; blocked with 20% fetal bovine serum (FBS) for 30 min; incubated with type I collagen primer antibody (1:3000 abcam, cat: 106017, UK) for 3 hrs at room temperature (the negative control was treated with PBS at this step); washed in TBS three times for 5 min each; incubated with a second antibody using LSAB system (Dako, cat: K0675 Denmark); the washing procedure was repeated; visualized with DAB kit (Dako, cat: K3468 Denmark), which stained the positive cells brown; and counterstained with haematoxylin.

Five high power views (400×) of each slide were randomly selected. The total cell number and type I collagen positive cells of each view were counted. The ratio was calculated y dividing the type I collagen positive cell number by the total cell number. The average of the five views was the final ratio of the slide.

Example 11

Experimental Design

Fifty rabbits were randomly allocated into five groups of ten (FIG. 1). The left rotator cuffs were fully dissected and reconstructed by one of the five methods. In situ reimplantation of dissected rotator cuff tendon served as the control. Five rabbits from each group were sacrificed at 4 and 8 weeks post-operatively.

A schematic of the rabbit massive rotator cuff tear model, used in this study, is depicted in FIG. 2. Autologous tenocytes enzyme digested from biopsy harvested from patellar tendon were cultivated in vitro and seeded on both bioscaffolds (cell density: $3.5 \times 10^6/cm^2$). When the cell-bioscaffolds were ready, the rotator cuff tendon was fully excised from the insertion point of the humeral tuberosity to the muscle-tendon junction creating a defect around 7×8 mm$^2$. In the control group, this was reimplanted into the excision site. In the other four groups, the excised tendon portion was discarded and replaced by ACI-Maix™ and Restore™ bioscaffolds, with or without autologous tenocytes.

Example 12

Protein and mRNA Expression of Type I/III and EphA4 in Tenocytes

Figure 3:
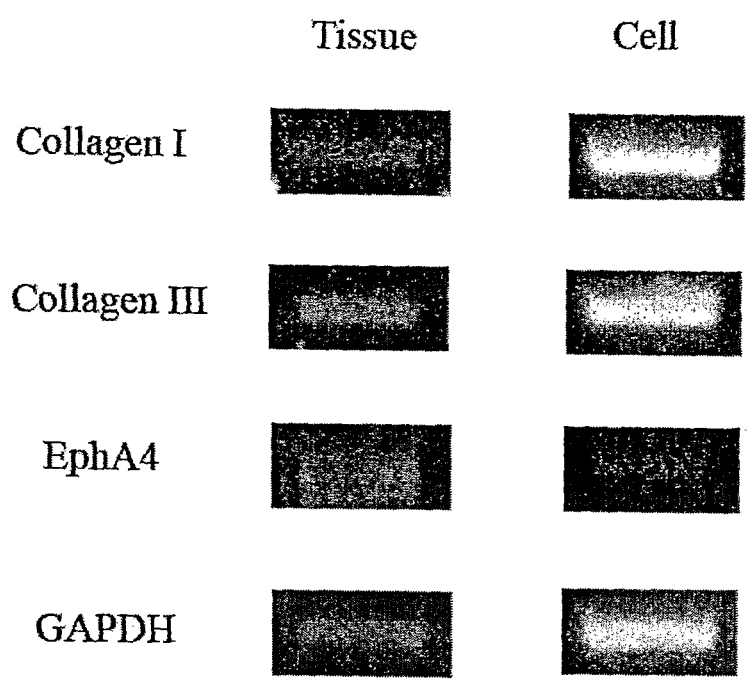
FIG. 3: Expression of type I/III collagen and EphA4 in cultured tenocytes and tendon tissue.

Using RT-PCR analyses, we compared the gene expression profiles of type I/III collagen and EphA4 in tendon tissue and cultured tenocytes. As shown in FIG. 3, tenocytes maintained their ability to express collagen types I/III and EphA4 mRNA in vitro. The level of expression appeared higher in mRNA samples extracted from the in vitro cultured tenocytes than that from tendon tissue when compared to house keeping gene GAPDH.

Figure 4:
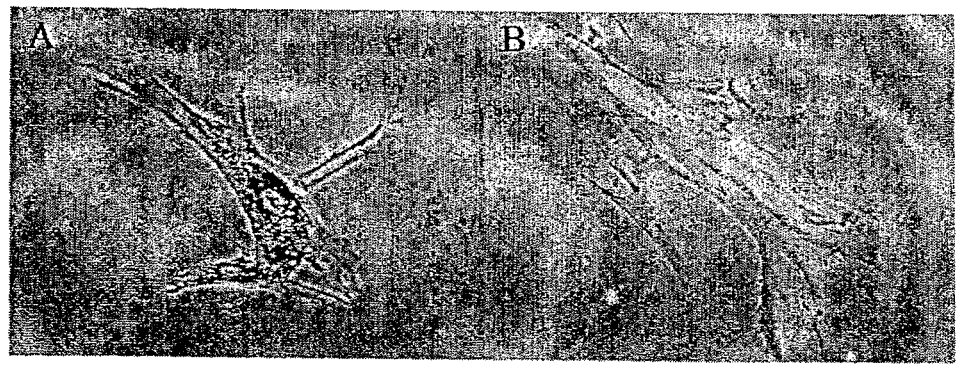
FIG. 4: Immunostaining for type I collagen on tenocytes in vitro culture. (A) Test well (100×); (B) control well (100×).

To further confirm if in vitro tenocytes produce type I collagen protein, immunohistochemical staining of type I protein was performed in the cultured tenocytes. The result shows that type I collagen protein in the cytoplasm of in vitro cultured tenocytes (FIG. 4A), while in the control well no positive staining was seen (FIG. 4B).

Example 13

Morphological Assessment of Tenocyte-Seeded Bioscaffolds

Figure 5:
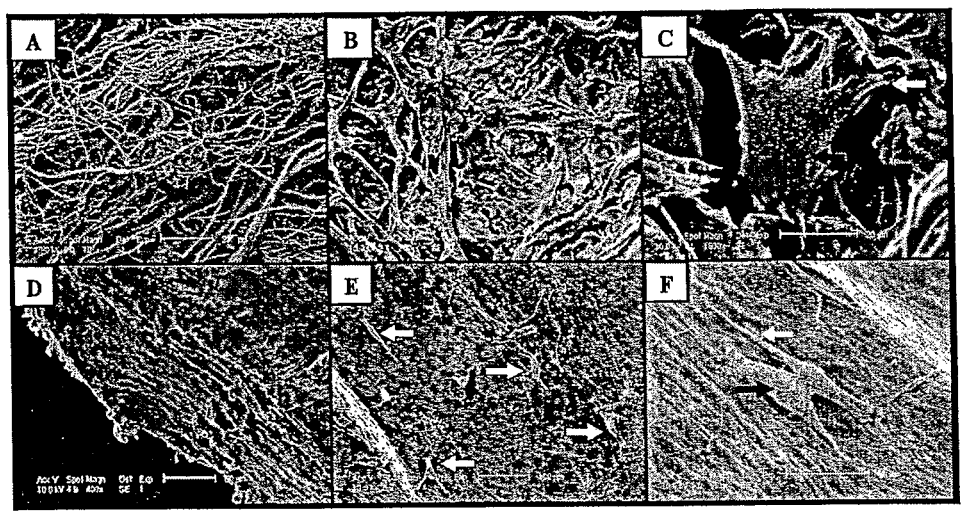
FIG. 5: (A) The loose, porous collagen fibre arrangement of the ACI-Maix™ bioscaffold (100×). (B) A sheet of tenocytes integrated within the ACI-Maix™ collagen fibres after 72 hour (200×). (C) Solo cell morphology demonstrated two types of protrusions (blebs: black arrow & lamellipodia: white arrow) on the ACI-Maix™ bioscaffold (1500×). (D) Cross-sectional scanning electron microscopy revealed the flat surface morphology and highly compact collagen structure of the Restore™ small intestine submucosa bioscaffold (400×). (E) Tenocytes (arrows) displayed a monolayer growth pattern on Restore™ bioscaffold similar to that seen in vitro, with a spindle-shaped appearance and bi- or tripolar lamellipodia cell attachment (200×). (F) An individual cell on the Restore™ bioscaffold with protrusion (blebs: black arrow & lamellipodia: white arrow) seen on the cell surface (650×).

Scanning electron microscope analysis of the ACI-Maix™ collagen bioscaffold indicated a loose, porous collagen fibre arrangement with pore size of approximately 200 μm (FIG. 5A). At 24 hrs tenocytes had adhered to the collagen matrix and formed a sheet-like arrangement. By 72 hrs, abundant tenocyte replication had occurred and cells covered most of the bioscaffold surface (FIG. 5B). Higher magnification (FIG. 5C) of individual cell morphology demonstrated two types of protrusions, blebs and lamellipodia, radiating from the cell surface. The Restore™ SIS bioscaffold was characterized by a flat surface topology and highly compact structure (FIG. 5D). The growth pattern of tenocytes on the Restore™ bioscaffold was similar to that in culture flask, displaying a flattened fibroblastic-like appearance. Tenocyte replication was relatively slow with a monolayer growth pattern (FIG. 5E). Higher magnification revealed that Restore™-seeded tenocytes (FIG. 5F) also put out large numbers of protrusions on the surface of the cell similar to that on ACI-Maix™ bioscaffold.

Example 14

Gross and Examination

Following surgery, all rabbits survived until scheduled euthanasia. There were no wound infections or any other complications observed. A limping gait from the operative forelimb was observed during the first weeks post surgery, and then normal gait returned at 2 weeks. Gross examination revealed that no pull-off or failure of tendon repair was observed in any sample at either time'point. The mean thickness, width and length of fifty normal rabbit rotator cuff tendon harvested from unoperated shoulder was 2.5+0.3 mm, 6.6+0.5 mm and 8.8+0.5 mm, respectively (FIG. 16). Generally, the average thickness samples at 4 weeks was significantly ($p<0.01$) thicker than normal tendon, while samples at 8 weeks were significantly ($p<0.01$) thinner than normal tendon. No difference in width was found between normal and repair tendon. Both 4 and 8 week repair tendons were significantly elongated (4-5.5 mm longer, $p<0.01$) compared to normal tendon (FIG. 16).

Example 15

Histological Assessment of Control Treatment

Figure 6:
FIG. 6: Control group; hematoxylin and eosin. (A) Four week control samples were characterized by an increase in cellularity and neoangiogenesis and alteration in the organization of collagen fibres (250×). (B) Bone trough (BT) of 4 week samples were characterized by increased cell population and the absence of mineralized zone (100×). (C) Eight week samples displayed a more organized structure with less cell density and uniformly arrayed parallel collagen fibre arrangement (100×). (D) Bone trough of 8 week samples demonstrated typical mature 4-zone structure (100×). MT: Mid-substance of regenerated tendon.

Autologous tendon repair at 4 weeks post-surgery was characterized by an increase in cellularity, neoangiogenesis, and alterations in the normal longitudinal arrangement of the collagen fibres (FIG. 6A). The collagen became wavier than that of normal tendon with some disorganized areas and slightly rounded tenocyte nuclei. The tendon-bone junction at the bone trough was fibrocartilage-like with large spherical cartilage cells filling the space, similar to the normal tendon-bone junction except with a dense cell population and an absence of mineralized osteoid matrix (FIG. 4B). By 8 weeks, samples displayed a more organized structure with normal cell density and shape, and a healthy parallel arrangement of reparative collagen fibres (FIG. 6C). The bone trough of the 8 week sample exhibited a more mature 4-zone formation and better integration with the bone marrow (FIG. 6D).

Example 16

Histological Assessment of Bioscaffolds WITHOUT Autologous Tenocytes

Figure 7:
FIG. 7: ACI-Maix™ bioscaffold group; hematoxylin and eosin. (A) Large portions of the ACI-Maix™ bioscaffold were not absorbed at 4 weeks, with obvious lymphocyte infiltration surrounding the bioscaffold (25×). (B) The absorbed area of 4 week samples demonstrated primary repair pattern characterized by rough collagen arrangement, increasing cellularity, and neoangiogenic formation (100×). (C) The bone trough of 4 week samples was dominated by repaired cartilage tissue, with dense fibrous tissue extending from the edge of the bone trough (100×). (D) Eight week samples displayed more organized structure (100×). (E) The bone trough formation was also mature. (F) Inductions of adipose tissue (arrows) in the mid substance of the regenerated tendon (100×) U: unabsorbed bioscaffold; L: lymphocytes invasion; A: absorbed area V: vascularised tissue.

ACI-Maix™ group: At 4 weeks post surgery, all ACI-Maix™ grafts implanted without autologous tenocytes displayed large portions of the bioscaffold that were not absorbed. In areas where the original structure of the bioscaffold remained, there were large number of lymphocytic cells seen within and surrounding the remaining bioscaffold (FIG. 7A). The areas where the graft was absorbed demonstrated a primary repair pattern characterized by roughly parallel collagen arrangement, increased cellularity and vascularisation (FIG. 7B). The bone trough was dominated by repaired cartilage tissue, with dense fibrous tissue extending from the edge of the bone trough (FIG. 7C). At 8 weeks, the implant site displayed more bundles of parallel collagen fibres; containing low density fibroblastic cells and reduced neoangiogenesis (FIG. 7D). Bone trough formation also matured as collagen fibre organization was remodelled and produced good integration with the cortical and cancellor bone (FIG. 7E). However, two out of the five samples still contained fragments of unabsorbed bioscaffold with obvious lymphocytic infiltration. Plus, inductions of adipose tissue in the mid-substance of the regenerated tendon were found in all five 8 week samples (FIG. 7F).

Figure 8:
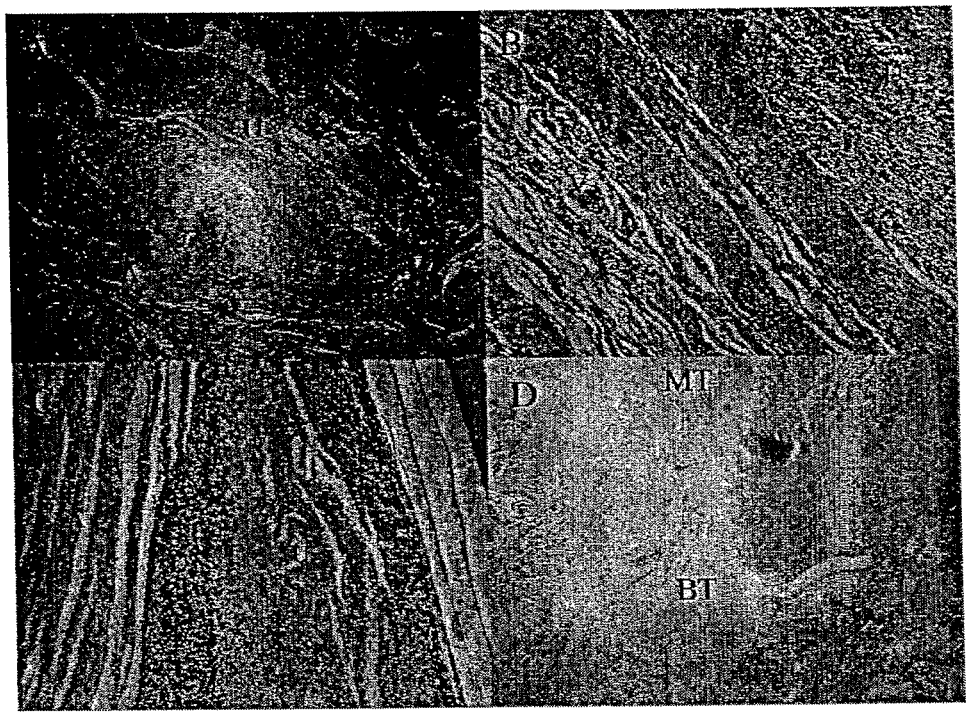
FIG. 8: Restore™ bioscaffold group; hematoxylin and eosin. (A) The original structure of the Restore™ SIS bioscaffold was seen as disorganized fibres. Numerous inflammatory cells were observed inside and around the implant (25×). (B) The absorbed area demonstrated increasing fibroblast number with both round and spindle shaped morphology present in a richly vascularised connective tissue matrix (100×). (C) An 8 week sample did not completely absorb and presented obvious lymphocyte infiltration (100×). (D) Bone tendon junction exhibited a mature 4-zone structure (100×). A: Absorbed area; U: unabsorbed bioscaffold; L: lymphocytes; V: vascularised tissue.

Restore™ group: In all five 4 week samples, Restore™ implanted without autologous tenocytes were only partially absorbed. The original structure of the Restore™ was present as disorganized bioscaffolds along the structure of tendon. Numerous inflammatory cells, predominantly lymphocytes, were observed at the margins of the graft (FIG. 8A). A few macrophages, plasma, eosinophil and polymorphic cells were occasionally spotted within the bioscaffold fibres. In areas where the Restore™ had been absorbed, large numbers of fibroblasts and lymphocytes were present within a richly vascularised connective tissue matrix resembling granulation tissue (FIG. 8B). The bone trough was occupied by fibrous tissue mixed with chondrocytes with the mineralized zone virtually absent in all samples.

At 8 weeks, four of the five Restore™ bioscaffold implants were totally absorbed. The one that wasn't completely absorbed presented obvious lymphocyte infiltration similar to 4 week samples (FIG. 8C). In the absorbed area, the collagen fibres were aligned in a less wavy pattern and angiogenesis was less intense. The tendon-bone junction exhibited a mature 4-zone structure including cortical bone, mineralized fibrocartilage; fibrocartilage and tendon (FIG. 8D). Some granulation tissue was spotted between the void of collagen fibres, resembling chronic granuloma response. Unexpectedly, some ectopic bone formation was found in the mid-substance of two samples.

Example 17

Histological Assessment of Bioscaffolds with Autologous Tenocytes

Figure 9:
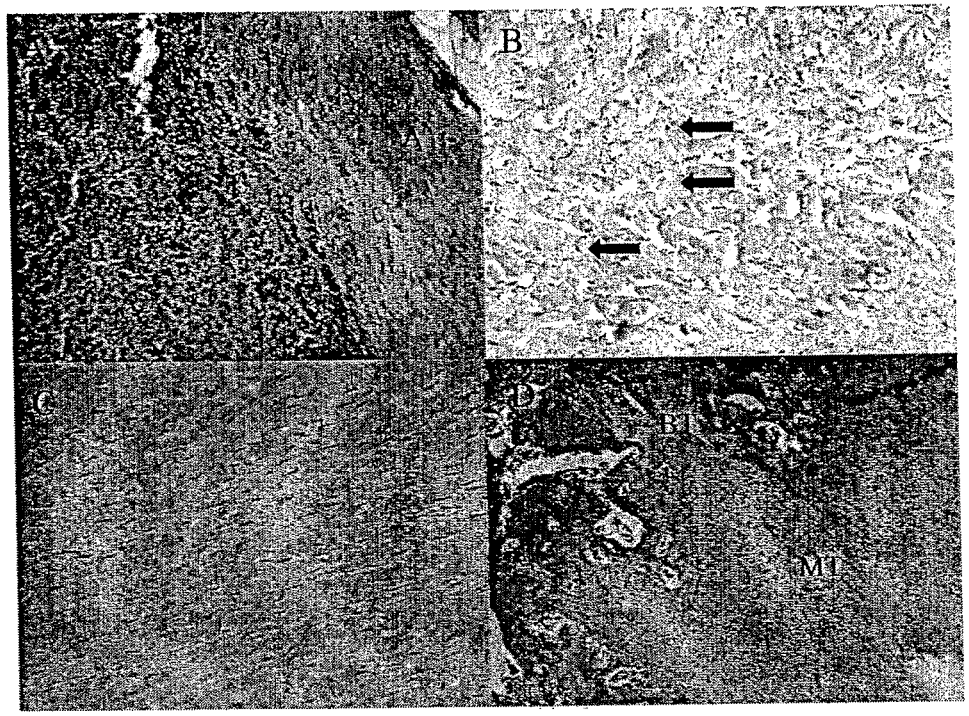
FIG. 9: ACI-Maix™ bioscaffold seeded with autologous tenocytes group; hematoxylin and eosin (A) At 4 weeks, ACI-Maix™ bioscaffold implanted with tenocytes was not fully absorbed and elicited lymphocytic cells infiltration (100×). (B) Few implanted autologous tenocytes (arrows) were also spotted within the remaining bioscaffold (200×). (C) At 8-weeks, ACI-Maix™ bioscaffold implanted with tenocytes displayed identical result as control group (100×). (D) The bone trough (BT) histology was indistinguishable from the control group (100×). A: Absorbed area; U: unabsorbed bioscaffold; L: lymphocytes; MT: Mid substance of regenerated tendon.

ACI-Maix™ group: At 4 weeks post surgery, both the neo-generated tendon and bone trough of ACI-Maix™ bioscaffold implanted with autologous tenocytes were similar to 4 week bioscaffolds implanted without tenocytes. Some portions of bioscaffold still remained and lymphocytic cells were again seen within and surrounding the bioscaffold (FIG. 9A). Implanted autologous tenocytes were also observed on the surface of unabsorbed bioscaffold (FIG. 9B). In areas where bioscaffold absorbed, rough collagen arrangement, and vascular beds were observed similar to other experimental groups.

Interestingly, at 8 weeks post implantation, superior reparative results were evidenced, with tendon histology similar to controls treatment (p>0.05) (FIG. 9C). All implanted bioscaffolds were fully absorbed and replaced by tendon tissue at 8 weeks. Collagen bundles were longitudinally arranged and the bone trough histological appearance was indistinguishable from the control histology (FIG. 9D). A slightly increased amount of fibroblasts were evenly distributed between bundles in a typically flattened, thin, and wavy pattern. Only one out of five samples contained adipose tissue in the middle of neo-generated tendon.

Figure 10:
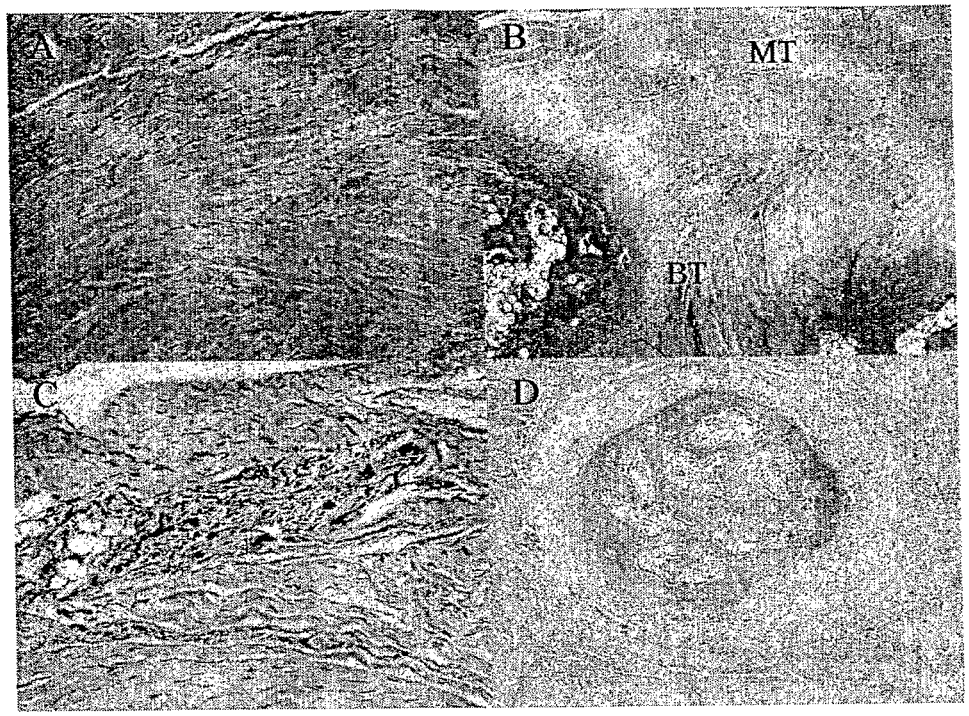
FIG. 10: Restore™ bioscaffold + autologous tenocytes group; hematoxylin and eosin. (A) At 8 weeks Restore™ bioscaffold implanted with autologous tenocytes demonstrated excellent tendon structure similar to control group (100×). (B) Tendon bone junction was also mature, displaying typical 4-zone structure (100×). (C) Some granulation tissue was spotted mixed with the collagen fibres, resembling chronic granuloma response (100×). (D) Small foci of ectopic bone were found in all groups that Restore™ bioscaffold was implanted (100×).

Restore™ group: Restore™ implanted with autologous tenocytes displayed a similar repair pattern to other groups at 4 weeks. Excellent reparative results were seen at 8 weeks, highlighted by histological appearance similar to control tendon repair, demonstrating longitudinally arranged collagen bundles with fibroblasts evenly distributed between the bundles in a spindle-shaped pattern (FIG. 10A) and mature bone trough formation (FIG. 10B). No unabsorbed bioscaffold was found in all five samples and most the bone trough formation demonstrated typical four zone structure. However, granulation tissue (FIG. 10C) was still observed in all 5 samples and ectopic bone (FIG. 10D) was found in 2 samples.

Example 18

Semi-Quantitative Assessment of Repair Tendon Histology

Figure 11:
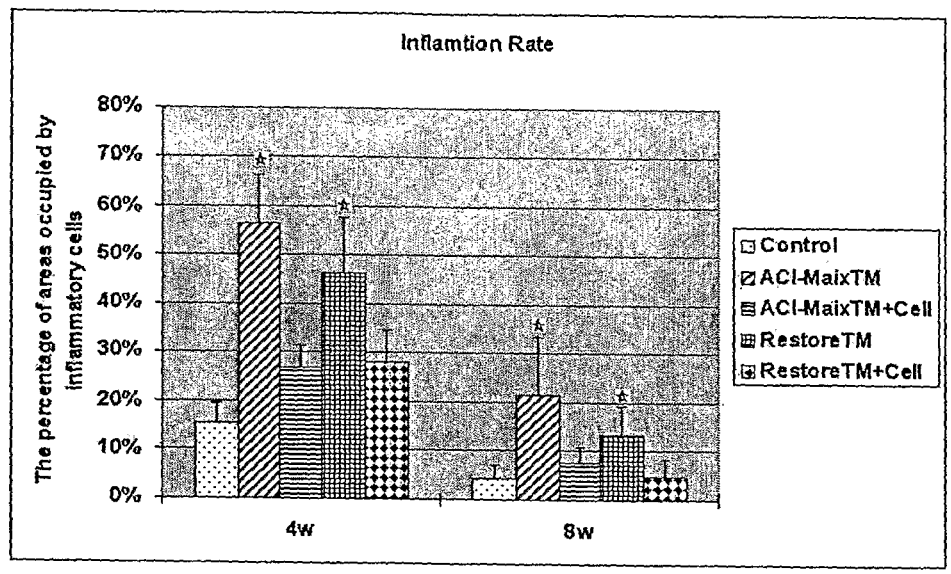
FIG. 11: Inflammation Rate: The percentage of repair tendon areas occupied by inflammatory cells.

Analysis of the inflammation rate to the bioscaffolds demonstrated that the inflammatory response was less intense in the bioscaffold-cell construct groups than in the bioscaffold-only (FIG. 11). At 4 weeks, the average inflammatory rate (the percentage of repair tendon areas occupied by inflammatory cells) was 56% with ACI-Maix™, whilst the ACI-Maix™+cell group was significantly (p<0.01) reduced to 26%. A similar phenomenon was observed in groups applying Restore™ bioscaffold, the inflammatory rate decreasing from 46% to 27% favouring autologous tenocytes implantation (p<0.05). However, when compared to the controls, the inflammatory rate in the four experimental groups was significantly (p<0.05) elevated, regardless with or without cell. At 8 weeks, the bioscaffold absorbed, and the inflammatory response of all groups was significantly (p<0.05) reduced compared to 4 weeks. In groups that autologous tenocytes were implanted, the inflammatory rates were very similar (p>0.05) to that of the control group, whilst the inflammation observed in bioscaffold-only group was still significantly (p<0.05) greater than controls.

Figure 12:
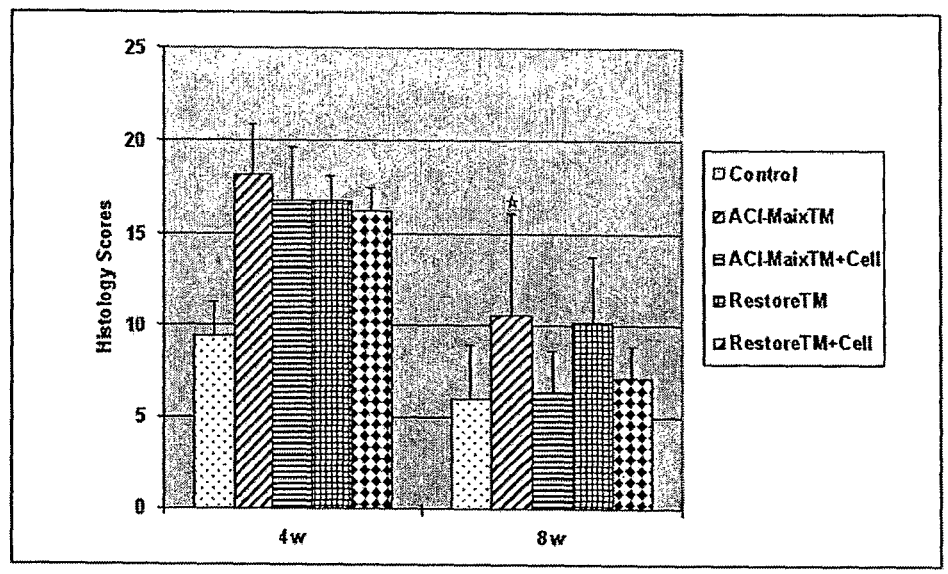
FIG. 12: Histology Scores for ACI-Maix™ and Restore™ bioscaffolds implanted alone or seeded with autologous tenocytes at 4 weeks and 8 weeks.

General histology examination revealed that, all experimental groups have poor histological scores compared to the positive control (p<0.01) at 4 weeks (FIG. 12). At 8 weeks, ACI-Maix™ bioscaffold implanted alone displayed significantly inferior histological score to the control (p<0.05), whilst seeded with autologous tenocytes it displayed much better score identical to the control (p>0.05). However, the difference between these two groups (ACI-Maix™ with and without tenocytes) was not significant (p>0.05). Although the histology score of Restore™ bioscaffold without tenocytes was worse than implanted with tenocytes and control, it still achieved an outcome not statistical significant different from either of them (p>0.05).

Figure 13:
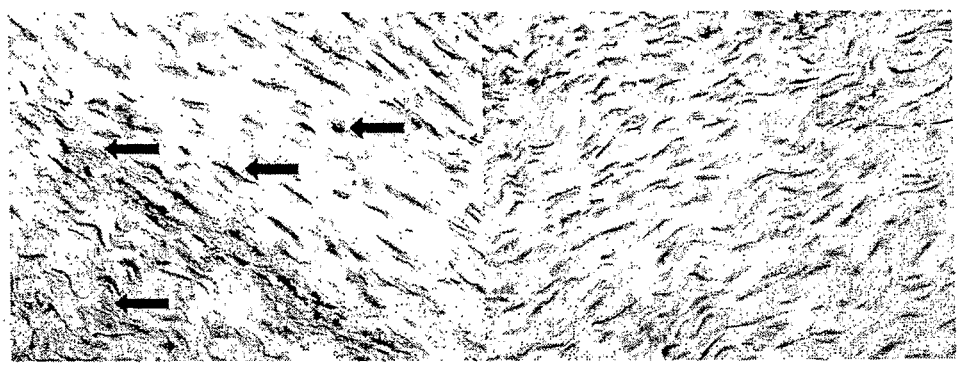
FIG. 13: Immunostaining of ACI-Maix™+tenocytes for type I collagen (A) Test (blue arrow: cytoplasm area; black arrow: extra cellular matrix) (400×). (B) Negative control (400×).
Figure 14:
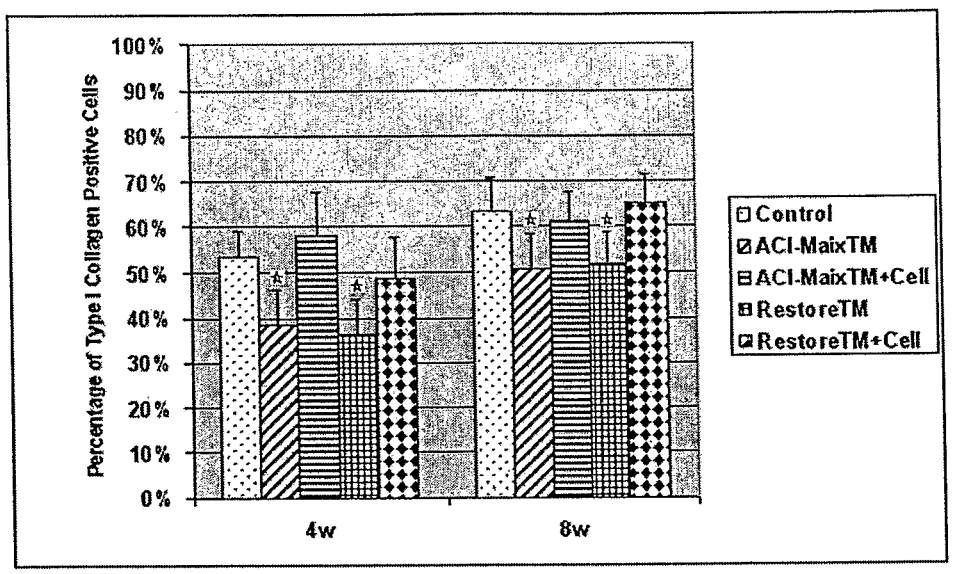
FIG. 14: Type I collagen positive cells in ACI-Maix™ and Restore™ bioscaffolds implanted alone or seeded with autologous tenocytes at 4 weeks and 8 weeks.

Immunostaining demonstrated that both cytoplasm and extra-cellular matrix were stained positive for type I collagen (FIG. 13A) while no positive staining was seen in the negative control (FIG. 13B). At 4 weeks, the average type I collagen positive cell ratio of the control group was 53.4%, ACI-Maix™ was 38.4%, ACI-Maix™ seeded with tenocytes was 58%, Restore™ was 36.2%, and Restore™ seeded with tenocytes was 48.8%. At 8 weeks, the type I collagen positive cell ratio slightly increased in all groups with the control group achieving 63.2%, ACI-Maix™ achieving 50.60%, ACI-Maix™ seeded with tenocytes achieving 61.2%, Restore™ achieving 51.80%, Restore™ seeded with tenocytes achieving 65%. At both time points, the positive rates of tenocytes seeded bioscaffolds were significantly higher than those without tenocytes (p<0.05, FIG. 14) and similar to the control (p>0.05).

The invention claimed is:

1. A method of treating rotator cuff tear in a mammalian subject in need thereof comprising the steps of:
   (i) selectively expanding tenocytes in vitro in a culture medium comprising:
      (a) at least 10% v/v serum;
      (b) insulin; and
      (c) betamethasone
      to produce a culture of expanded tenocytes;
   (ii) seeding a bioscaffold with said expanded tenocytes to produce a tenocyte seeded bioscaffold; and
   (iii) implanting said tenocyte seeded bioscaffold proximal to the rotator cuff tear.

2. The method of claim 1, wherein said rotator cuff tear is a massive rotator cuff tear.

3. The method of claim 1, wherein said tenocytes are isolated from a tenocyte-containing tissue before selective expansion.

4. The method of claim 3, wherein said tenocyte-containing tissue is a tendon.

5. The method of claim 1, wherein said tenocytes are from a mammalian animal selected from the group consisting of a sheep, a cow, a pig and a human.

6. The method of claim 5, wherein said mammalian animal is a human.

7. The method of claim 1, wherein said tenocytes are autologous.

8. The method of claim 1, wherein said culture medium comprises about 0.0006% w/v insulin and about 0.0002% w/v betamethasone.

9. The method of claim 1, wherein said culture of expanded tenocytes comprises at least 80% tenocytes.

10. The method of claim 1, wherein said culture of expanded tenocytes comprises at least 80% tenocyte cells that express one or more genes encoding the following: type I collagen, type III collagen, EphA4, scleraxis, Six1, COMP and Cbfa1.

11. The method of claim 1, wherein said tenocyte-seeded bioscaffold is cultured in vitro for a sufficient time to establish the tenocytes before implantation.

12. The method of claim 1, wherein said mammalian subject is a human.

13. The method of claim 1, wherein said bioscaffold comprises a matrix, a membrane, a microbead, a fleece, a thread, a gel, or mixtures thereof.

14. The method of claim 1, wherein said bioscaffold comprises a type I/III collagen matrix or a small intestinal submucosa.

15. The method of claim 1, wherein the step of seeding a bioscaffold with said expanded tenocytes to produce a tenocyte seeded bioscaffold is carried out at a cell density of 0.05 to 5 times the physiological cell density of native tendon.

16. The method of claim 15, wherein the cell density is at least $1 \times 10^6$ to $1 \times 10^7$ cells per cm$^2$.

17. The method of claim 15, wherein the cell density is $4 \times 10^6$ cells per cm$^2$.

18. The method of claim 1, wherein said culture medium comprises at least 15% v/v serum.

19. A method of treating massive rotator cuff tear in a human subject in need thereof comprising the steps of:
   (i) isolating tenocytes from tendon tissue isolated from said subject;
   (ii) selectively expanding the isolated tenocytes in vitro in a culture medium comprising:
      (a) at least 10% v/v serum;
      (b) about 0.0006% w/v insulin; and
      (c) about 0.0002% w/v betamethasone
      to produce a culture of expanded tenocytes comprising at least 80% tenocytes;
   (iii) seeding a bioscaffold with said expanded tenocytes and culturing said bioscaffold and tenocytes for no more than five days to produce a tenocyte-seeded bioscaffold; and
   (iv) implanting said tenocyte-seeded bioscaffold into the rotator cuff tear and securing with sutures.

20. The method of claim 19, wherein said bioscaffold comprises a matrix, a membrane, a microbead, a fleece, a thread, a gel, or mixtures thereof.

21. The method of claim 19, wherein said bioscaffold comprises a type I/III collagen matrix or a small intestinal submucosa.

22. The method of claim 19, wherein the step of seeding a bioscaffold with said expanded tenocytes to produce a tenocyte seeded bioscaffold is carried out at a cell density of 0.05 to 5 times the physiological cell density of native tendon.

23. The method of claim 22, wherein the cell density is at least $1 \times 10^6$ to $1 \times 10^7$ cells per cm$^2$.

24. The method of claim 22, wherein the cell density is $4 \times 10^6$ cells per cm$^2$.

25. The method of claim 19, wherein said culture medium comprises at least 15% v/v serum.

26. A method of treating a massive rotator cuff tear in a human subject in need thereof comprising the steps of:
   (i) isolating tenocytes from tendon tissue isolated from said subject;
   (ii) selectively expanding the isolated tenocytes in vitro in a culture medium comprising:
      (a) at least 15% v/v serum;
      (b) about 0.0006% w/v insulin; and
      (c) about 0.0002% w/v betamethasone
      to produce a culture of expanded tenocytes comprising at least 80% tenocytes;
   (iii) seeding a bioscaffold with said expanded tenocytes to a cell density of $4 \times 10^6$ cells per cm$^2$ and culturing said bioscaffold and tenocytes for no more than five days in said culture medium to produce a tenocyte-seeded bioscaffold; and
   (iv) implanting said tenocyte-seeded bioscaffold into the rotator cuff tear and securing with sutures.

* * * * *